United States Patent [19]

Steiner et al.

[11] Patent Number: 5,499,984
[45] Date of Patent: Mar. 19, 1996

[54] UNIVERSAL MODULAR REAMER SYSTEM

[75] Inventors: Anton J. Steiner, Wharton; David A. Landspurg, Kinnelon, both of N.J.; Robert A. Winquist, Seattle, Wash.

[73] Assignee: Snap-on Incorporated, Kenosha, Wis.

[21] Appl. No.: 224,046

[22] Filed: Apr. 7, 1994

[51] Int. Cl.⁶ ............................................. A61B 17/16
[52] U.S. Cl. ...................... 606/80; 606/79; 408/713
[58] Field of Search .................. 606/79, 80, 81, 606/91; 403/326, 329, 289, DIG. 4; 408/276, 713; 211/69, 60.1

[56] References Cited

U.S. PATENT DOCUMENTS

| | | |
|---|---|---|
| 2,747,384 | 5/1954 | Beam . |
| 2,929,510 | 3/1960 | Penn ........................ 211/60 R |
| 3,367,326 | 2/1968 | Frazier . |
| 3,554,192 | 1/1971 | Isberner . |
| 4,131,116 | 12/1978 | Hedrick ........................ 606/81 |
| 4,304,523 | 12/1981 | Corsmeier et al. ............ 403/326 |
| 4,541,423 | 9/1985 | Barber . |
| 4,706,659 | 11/1987 | Matthews et al. . |
| 4,751,922 | 6/1988 | DiPietropolo . |
| 4,781,181 | 11/1988 | Tanguy . |
| 4,813,808 | 3/1989 | Gehrke ........................ 403/326 |
| 4,880,122 | 11/1989 | Martindell ..................... 211/69 |
| 5,108,405 | 4/1992 | Mikhail et al. . |
| 5,230,348 | 7/1993 | Ishibe et al. . |
| 5,269,785 | 12/1993 | Bonutti . |
| 5,330,480 | 7/1994 | Meloul et al. .................. 606/80 |

FOREIGN PATENT DOCUMENTS

| | | |
|---|---|---|
| 2366826 | 4/1977 | France . |
| 2542056 | 3/1977 | Germany . |

Primary Examiner—Stephen C. Pellegrino
Assistant Examiner—Scott Markow
Attorney, Agent, or Firm—Emrich & Dithmar

[57] ABSTRACT

A medullary reaming system includes a flexible, hollow, tubular shaft formed of a nickel-titanium alloy having one end coupled to a rotary drive and having the other end coupled to a cutting head by means of a male connector on the shaft engageable in a female connector on the head. The female connector is a tubular shank with diametrically opposed slots in the outer surface thereof, while the male connector has flexible arms with latch tabs engageable in the slots to latch the head to the shaft. A support has a plurality of notches for respectively storing cutting heads. The head shank is received in the notch with the notch edges received in the shank slots, so that when the male connector on the shaft is inserted into the shank the notch edges prevent latching of the head to the shaft until the head is removed from the support.

7 Claims, 1 Drawing Sheet

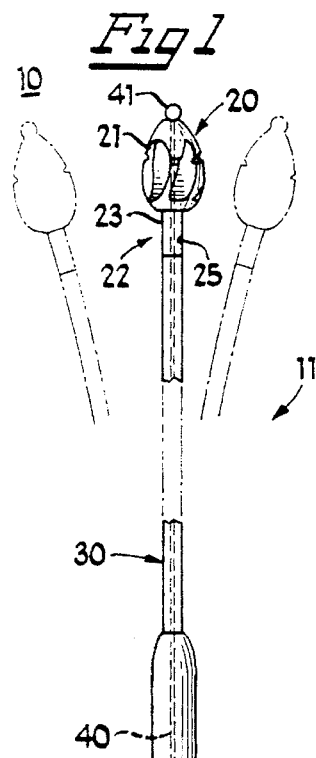
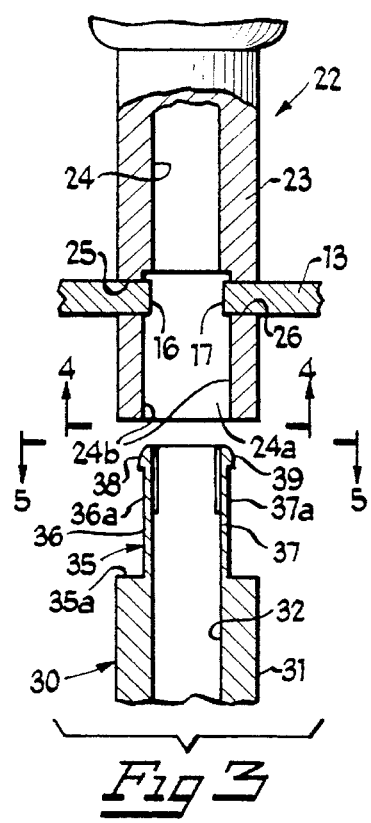
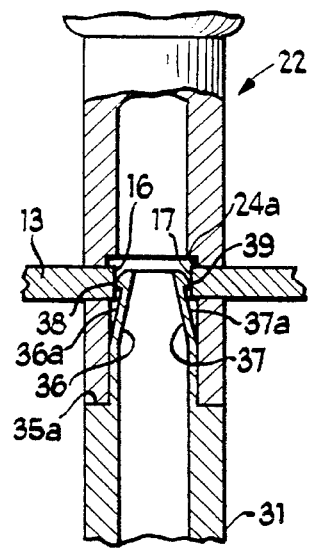
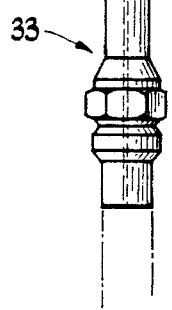
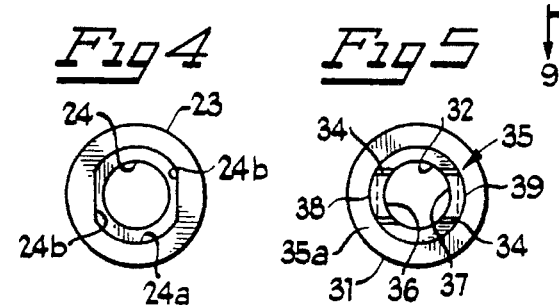
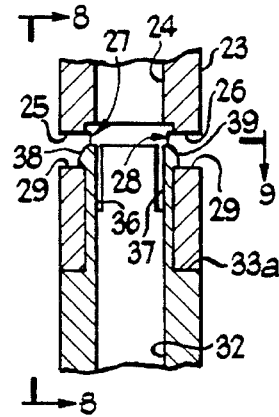
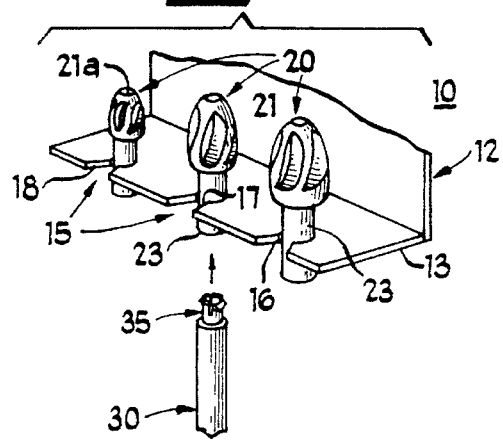
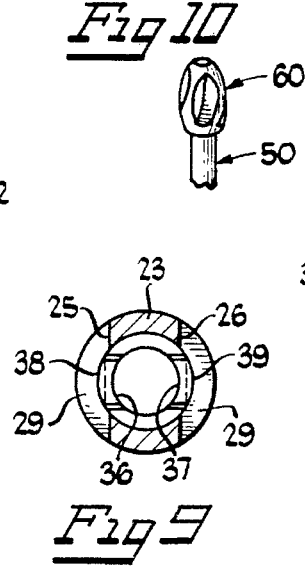
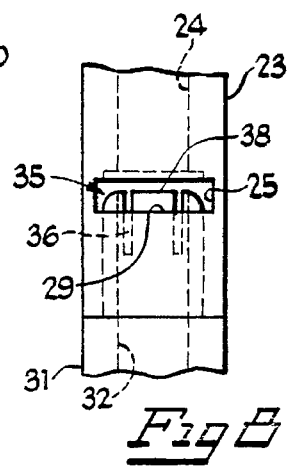

5,499,984

UNIVERSAL MODULAR REAMER SYSTEM

BACKGROUND OF THE INVENTION

1. Field of the Invention

The invention relates to medullary reaming systems and to flexible drive shafts therefor.

2. Description of the Prior Art

Medullary reamers are used to enlarge the medullary canals of bone for various reasons. The medullary canals of bone typically have some degree of curvature and, for this reason, are almost always prepared with reamers having a flexible shaft.

One type of prior flexible medullary reamer shaft consists of a spiral or helically wound metal wire or strip which comprises the shaft of the reamer. A disadvantage of this type of shaft is that the reamer can be operated only in the forward mode of rotation. If the reamer is reversed, which is occasionally necessary in order to free a lodged reamer, for example, the shaft unwinds, damaging the shaft. Another disadvantage of this spiral shaft design is that the voids between the shaft coils can trap blood and tissue, making it extremely difficult to thoroughly and properly clean and sterilize the shaft after use. Another disadvantage is that if the cutting head experiences unusually high resistance, the driving torque will accumulate in the shaft as its coils close and then, when it overcomes the resistance to the head, will be released in a sudden burst, causing the cutting head to jump or spin ahead rapidly in an uncontrolled fashion. Such irregular movement of the cutting head may damage the bone.

Another type of medullary reamer shaft comprises a plurality of parallel, flexible elements joined together at their opposite ends by means of a welded or soldered connection. Such a shaft construction suffers from most of the same disadvantages as the helically coiled shaft described above. Another disadvantage occurs in attempting to utilize the central bore of the reamer, to receive a long, small diameter guide wire, which had previously been inserted into the medullary canal to act as a track for the advancing reamer. Except at its respective ends, this parallel-element reamer shaft lacks a well-defined and bordered central bore, making it difficult to prevent the guide wire from exiting the reamer in the area of the free standing shaft wires during the initial positioning of the guide wire within the reamer.

To overcome many of these disadvantages, there has also been provided a hollow tubular shaft formed of synthetic plastic material or a fiber-reinforced composite material. However, plastic shafts may lack the necessary torsional strength. Also, the reamer is autoclaved often and plastic will ultimately fail. A disadvantage of fiber-reinforced composite shafts is that, on failure, there is a danger that fibers will enter the blood stream.

Also, in prior medullary reamers the cutting head has been fixed to the flexible shaft, permanently by suitable bonding or the like. Thus, the head and the shaft form an integral unit and, when it is desired to use a different size cutting head, an entire reaming unit must be substituted. It is known to attach cutting heads to the shaft by suitable fasteners, such as a set screw, but this requires handling and the use of suitable tools.

SUMMARY OF THE INVENTION

It is a general object of the invention to provide an improved medullary reaming system which avoids the disadvantages of prior systems while affording additional structural and operating advantages.

An important feature of the invention is the provision of a medullary reamer with a flexible drive shaft which provides uniform transmission of energy to a cutting head in forward and reverse directions and which is easy to clean.

In connection with the foregoing feature, a further feature of the invention is the provision of a reamer shaft of the type set forth which minimizes the risk of body contamination.

Another feature of the invention is the provision of a reaming system which permits quick and easy mounting of any of a plurality of different cutting heads on a shaft without the use of tools and without manual handling of the cutting head In connection with the foregoing feature, a further feature of the invention is the provision of a reaming system of the type set forth which affords automatic releasable latching of a cutting head to the shaft.

Certain ones of these and other features of the invention are attained by providing in a medullary rotational reamer having a flexible shaft with a cutting head at one end and an adaptor piece at its opposite end for connecting the shaft to a rotational drive element thereby causing rotation of the shaft, the improvement comprising: the flexible shaft being comprised of a metal alloy including titanium.

Still other features of the invention are attained by providing a modular medullary rotational reaming system comprising: a flexible shaft having a drive coupling portion at one end thereof for connecting the shaft to a rotational drive element to cause rotation of the shaft and, a first head coupling portion at the other end thereof, first latch structure on the first head coupling portion movable between latching and unlatching conditions, a cutting head having a second head coupling portion thereon including second latch structure, and a support for storing the cutting head in a supported position readily accessible to a user, the first and second head coupling portions being mateably engageable with each other in a coupled condition for interconnecting the head and the shaft, the support being engageable with the first latch structure for holding it in its unlatching condition when the first and second head coupling portions are engaged in their coupled condition while the cutting head is held on the support, the first latch structure being responsive to removal of the cutting head from the support while the first and second head coupling portions are engaged in their coupled condition for moving to the latching condition, thereby to latch the cutting head to the shaft.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWINGS

For the purpose of facilitating an understanding of the invention, there is illustrated in the accompanying drawings a preferred embodiment thereof, from an inspection of which, when considered in connection with the following description, the invention, its construction and operation, and many of its advantages should be readily understood and appreciated.

FIG. 1 is a fragmentary, side elevational view of the reamer of a medullary reaming system in accordance with the present invention, with portions broken away and showing different positions in phantom to illustrate the flexibility of the shaft;

FIG. 2 is a fragmentary, perspective view of the support of the reaming system holding a plurality of cutting heads and illustrating insertion of the reamer shaft;

FIG. 3 is an enlarged, fragmentary view in partial vertical section showing the female connector of a cutting head held on the support with the male connector on the shaft about to be inserted;

FIG. 4 is an end view of the female connector taken along the line 4—4 in FIG. 3;

FIG. 5 is an end view of the male connector taken along the line 5—5 in FIG. 3;

FIG. 6 is a view similar to FIG. 3, illustrating the male and female connectors in their coupled condition;

FIG. 7 is a view similar to FIG. 6, illustrating the latching engagement of the male and female connectors after removal from the support;

FIG. 8 is a fragmentary, side elevational view taken along the line 8—8 in FIG. 7;

FIG. 9 is a sectional view taken along the line 9—9 in FIG. 7; and

FIG. 10 is a fragmentary perspective view of a reamer with a fixed cutting head.

DESCRIPTION OF THE PREFERRED EMBODIMENT

Referring to FIGS. 1 and 2, there is illustrated a reaming system 10 in accordance with the present invention. The system 10 includes a reamer 11, comprising a cutting head 20 fixed to the end of a flexible shaft 30, and a support 12 adapted for holding a plurality of heads 20 in a support position for ready access by a user. Referring to FIG. 2, the support 12 includes a bracket 13 which may be in the form of a flat plate having a plurality of support notches 15 formed therein. Each of the notches 15 has a part-circular inner end and a pair of parallel notch edges 16 and 17 which have outwardly tapered portions 18 at their outer ends. Each of the cutting heads 20 has a head body 21, which is a toothed or fluted cutting element having an axial bore 21a therethrough. Integral with the head body 21 at its tail end is a coupling portion in the nature of a female connector 22, which is preferably in the form of a cylindrical tubular coupling shank 23. Referring also to FIGS. 3, 4 and 7, the coupling shank 23 has an axial bore 24 therethrough with an enlarged-diameter counterbore 24a at its distal end, the counterbore 24a being provided with parallel flats 24b along diametrically opposite sides thereof. Respectively formed in the coupling shank 23 at diametrically opposed locations adjacent to the flats 24b are lateral slots or grooves 25 and 26, which are formed as chords of the coupling shank 23 and are sufficiently deep to communicate with the counterbore 24a adjacent to its inner end for respectively defining radial apertures 27 and 28 (FIG. 7). The lower sides of the slots or grooves 25 and 26, as viewed in FIG. 7, form latch keeper shoulders 29 for a purpose to be explained more fully below.

Referring also to FIGS. 5, 6, 8 and 9, the flexible shaft 30 is in the nature of a cylindrical tubular member having a cylindrical outer surface 31 and an axial bore 32 therethrough. The shaft 30 may have any desired length, depending upon the particular application, but may typically be in the range of from 12 to 20 inches. It is a significant aspect of the invention that the shaft 30 is formed of a titanium alloy and, more specifically, of a nickel-titanium alloy of a type which has considerable flexibility. Preferably, the nickel-titanium alloy is "super elastic" alloy having a maximum recoverable strain of approximately 8%, i.e., the material can be strained up to 8% and will still elastically return to its original configuration. There results a flexible shaft 30 which has great torsional strength and yet provides the flexibility necessary for medullary reaming operations. The monolithic metal structure precludes any release of fibrous material or the like in the event of failure of the shaft. In a constructional model of the invention, the flexible shaft 30 is formed of a nickel-titanium alloy of the type sold by Raychem under the designation TINEL® Alloy BB.

The flexible shaft 30 is coupled at one end thereof by a drive coupler or adaptor 33 to an associated source of rotational drive power (not shown) for rotating the shaft about its axis, all in a known manner. Integral with the shaft 30 at its other end and projecting axially therefrom is a coupling structure in the nature of a male connector 35 of reduced cross-sectional area, so that the connector 35 cooperates with the adjacent end of the shaft 30 to define therebetween an annular shoulder 35a. The male connector 35 is basically cylindrical in shape and has a pair of parallel slots 34 extending thereacross at the distal end thereof as chords thereof, thereby to form two diametrically flexible arms 36 and 37, respectively having flattened outer surfaces 36a and 37a along most of their length. The flattened surfaces 36a and 37a terminate short of the distal ends of the arms 36 and 37 so as to define laterally outwardly projecting latch fingers or tabs 38 or 39, respectively, on the arms 36 and 37.

In operation, a plurality of the cutting heads 20 are preferably supported on the support 12, as illustrated in FIG. 2. The cutting heads 20 all have identical coupling shanks 23, but may have different size head bodies 21. The coupling shanks 23 are respectively received in the support notches 15. The notch edges 16 and 17 are spaced apart a distance less than the outer diameter of the coupling shank 23 and are respectively received in the lateral slots or grooves 25 and 26 of the coupling shank 23, as is best illustrated in FIGS. 2, 3 and 6. The distance between the notch edges 16 and 17 is such that, in this supported position, they will respectively extend radially inwardly of the coupling shank 23 at least as far as the flats 24b. It will be appreciated that, when the cutting heads 20 are thus supported on the support 12, they are effectively restrained against axial movement. While, in the illustrated embodiment, the support 12 is oriented so that the supported coupling shanks 23 are disposed substantially vertically, it will be appreciated that other orientations could be used for ease of access, depending upon the particular application.

When a user wishes to attach a particular cutting head 20 to the flexible shaft 30, the male connector 35 is aligned beneath the selected cutting head 20, as illustrated in FIGS. 2 and 3, and is rotationally oriented so that the flexible arms 36 and 37 are, respectively, aligned beneath the flats 24b of the coupling shank 23. The male connector 35 is then inserted into the female connector 22 in the direction of the arrow in FIG. 2 to the coupled condition illustrated in FIG. 6, wherein the distal end of the coupling shank 23 bottoms against the shoulder 35a on the shaft 30. It will be appreciated that the arms 36 and 37 will flex to permit their insertion into the counterbore 24a of the coupling shank 23 and, as was indicated above, the support bracket 13 will firmly hold the cutting head 20 against axial movement in response to this insertion. In the coupled condition of FIG. 6, the latch fingers or tabs 38 and 39 will be respectively disposed opposite the lateral slots or grooves 25 and 26 in the coupling shank 23, but will be deflected out of those slots or grooves to an unlatching condition shown in FIG. 6, wherein they are prevented from engagement in the slots 25 and 26 by the notch edges 16 and 17 of the support bracket 13.

When the parts have been joined in the coupled condition illustrated in FIG. 6, the user then pulls the flexible shaft 30 laterally outwardly to remove the cutting head 20 from the support bracket notch 15. As the coupling shank 23 clears the notch 15, the flexible arms 36 and 37 resiliently snap back to their normal latching conditions, moving the latch fingers or tabs 38 and 39 respectively into latching engagement with the latch keeper shoulders 29, as illustrated in FIGS. 7–9, thereby firmly latching the cutting head 20 to the flexible shaft 30.

It will be appreciated that, when it is desired to change cutting heads, the user simply moves the coupling shank 23 of the coupled cutting head 20 back into its supported position in the corresponding notch 15 in the support bracket 13. As the notch edges 16 and 17 reenter the lateral slots or groove 25 and 26 on the coupling shank 23 they deflect the flexible arms 36 and 37 back to their unlatching conditions illustrated in FIG. 6, thereby permitting easy removal of the male connector 35 from the female connector 22 for reattachment to another cutting head 20.

It can be seen that the axial bore 32 through the flexible shaft 30 continues through the male connector 35, and the axial bore 24 through the coupling shank 23 is continuous with the axial bore 21a through the cutting head body 21. Thus, when the cutting head 20 is mounted on the flexible shaft 30, as is illustrated in FIG. 1, there is a continuous axial bore through the entire assembly, in standard fashion, for accommodating a guide wire 40. In use, as the reamer 11 is passed through a medullary canal it is slid along the guide wire 40 which has been preinserted in the canal, the guide wire 40 having an enlarged knob 41 at its distal end sized so as not to pass through the axial bore in the reamer 11, for purposes of retrieving the reamer, all in a known manner.

While, in the preferred embodiment, the cutting heads 20 are removably coupled to the flexible shaft 30, it will be appreciated that the flexible shaft of the invention could be provided with a fixed cutting head. Thus, in FIG. 10 there is shown a flexible shaft 50, which may be the same as the shaft 30 except that it lacks the male connector 35, to which a cutting head 60 is fixedly Secured by any suitable means.

From the foregoing, it can be seen that there has been provided an improved reaming system which has a reamer with a flexible shaft of great torsional strength while minimizing the chance of contamination and, at the same time, is modular so as to provide a simple and effective means for removably connecting the reamer shaft to a selected one of a plurality of different cutting heads without the use of tools.

We claim:

1. A modular medullary rotational reaming apparatus comprising: a flexible shaft having a drive coupling portion at one end thereof for connecting said shaft to a rotational drive element to cause rotation of the shaft and having a first head coupling portion at the other end thereof, first latch structure on said first head coupling portion movable between latching and unlatching conditions; means biasing said first latch structure to the latching condition; a cutting head having a second head coupling portion thereon including second latch structure; and a support for storing said cutting head in a supported position readily accessible to a user; one of said head coupling portions including a socket having an axis and the other of said head coupling portions including a plug axially receivable in said socket, said first and second head coupling portions being non-rotationally mateably engageable with each other in a coupled condition for interconnecting said head and said shaft, said support including retaining means engageable with said first latch structure for holding it in its unlatching condition when said first and second head coupling portions are engaged in their coupled condition while said cutting head is held on said support, said first latch structure being responsive to removal of said cutting head from said support while said first and second head coupling portions are engaged in their coupled condition for moving to the latching condition, thereby to latch said cutting head to said shaft.

2. The reaming apparatus of claim 1, wherein said first latch structure includes a resilient flexible arm having a latch finger thereon, said second latch structure comprising a latch keeper engageable by said latch finger.

3. The reaming apparatus of claim 2, wherein said second head coupling portion includes a tubular shank projecting from said head, said second latch structure including a radial aperture formed in said shank.

4. The reaming apparatus of claim 3, wherein said shank has a slot formed in the outer surface thereof and communicating with said radial aperture, said support having a notch formed therein and defining a notch edge, said shank being receivable in said notch when said cutting head is disposed in said supported position with said notch edge disposed in said slot for preventing axial movement of said cutting head and for preventing engagement of said latch finger in said radial aperture.

5. The reaming apparatus of claim 1, wherein said support includes means for storing a plurality of cutting heads in supported positions readily accessible to a user.

6. The reaming apparatus of claim 1, wherein said support includes means engageable with said cutting head in its supported position for preventing axial movement of said head.

7. The reaming apparatus of claim 1, wherein said shaft is formed of a nickel-titanium alloy.

* * * * *